US012758740B2

(12) United States Patent
Mejia-Suarez et al.

(10) Patent No.: US 12,758,740 B2
(45) Date of Patent: Oct. 13, 2026

(54) APPARATUS FOR RETAINING AND SEALING SEPTUM IN INSERTION MECHANISM FOR FLUID DELIVERY DEVICE

(71) Applicant: Becton, Dickinson and Company, Franklin Lakes, NJ (US)

(72) Inventors: Laura Mejia-Suarez, Allston, MA (US); Alexander Segit, Eliot, ME (US); Nitish Kunaparaju, Burlington, MA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1158 days.

(21) Appl. No.: 17/838,938

(22) Filed: Jun. 13, 2022

(65) Prior Publication Data

US 2022/0409856 A1 Dec. 29, 2022

Related U.S. Application Data

(60) Provisional application No. 63/214,480, filed on Jun. 24, 2021.

(51) Int. Cl.
*A61M 39/00* (2006.01)
*A61M 5/158* (2006.01)
(Continued)

(52) U.S. Cl.
CPC ........ *A61M 25/0097* (2013.01); *A61M 5/158* (2013.01); *A61M 25/0625* (2013.01);
(Continued)

(58) Field of Classification Search
CPC .............. A61M 39/06; A61M 39/0606; A61M 39/0613; A61M 2039/062;
(Continued)

(56) References Cited

U.S. PATENT DOCUMENTS 4,802,885 A * 2/1989 Weeks .............. A61M 39/0208 604/132
5,312,363 A * 5/1994 Ryan ..................... A61M 39/06 604/167.04
(Continued)

FOREIGN PATENT DOCUMENTS

CA 2382225 A1 3/2001
CN 109156942 A 1/2019
(Continued)

OTHER PUBLICATIONS

"Medical Applications of Stainless Steel 304"; Aug. 30, 2012; retrieved from https://www.azom.com/article.aspx?ArticleID=6641. (Year: 2012).*

*Primary Examiner* — Nathan R Price
(74) *Attorney, Agent, or Firm* — Dickinson Wright PLLC

(57) ABSTRACT

An improved wedge is provided for a septum and wedge subassembly in a fluid path of a fluid delivery device such as for use in a catheter insertion mechanism of a patch pump. The wedge has a retaining edge to provide axial force to retain a septum therein to obviate need for additional insertion mechanism components to retain the septum in place as a needle passes therethrough to facilitate insertion of a catheter and then retracts. The retaining edge can be rolled or flanged to extend at least partially over a surface of the septum. The wedge is also configured to provide radial compression on the septum to achieve a sufficient needle and septum interface seal to withstand a filling pressure of the fluid delivery device.

20 Claims, 13 Drawing Sheets

(51) Int. Cl.
*A61M 25/00* (2006.01)
*A61M 25/06* (2006.01)
*A61M 5/142* (2006.01)

(52) U.S. Cl.
CPC .................... *A61M 5/14248* (2013.01); *A61M 2005/14252* (2013.01); *A61M 2005/1583* (2013.01); *A61M 2005/1585* (2013.01); *A61M 2005/1586* (2013.01); *A61M 25/0606* (2013.01); *A61M 2039/0072* (2013.01)

(58) Field of Classification Search
CPC .. A61M 2039/0626; A61M 2039/0633; A61M 2039/0226; A61M 2039/0072
See application file for complete search history.

(56) References Cited

U.S. PATENT DOCUMENTS

| | | | | | |
|---|---|---|---|---|---|
| 6,056,718 | A * | 5/2000 | Funderburk | A61M 25/0097 | 604/93.01 |
| 7,985,199 | B2 * | 7/2011 | Kornerup | A61M 39/02 | 604/93.01 |
| 8,226,614 | B2 * | 7/2012 | Turner | A61M 5/168 | 604/164.04 |
| 2003/0181878 | A1 * | 9/2003 | Tallarida | A61M 39/0208 | 604/288.04 |
| 2008/0243085 | A1 * | 10/2008 | DeStefano | A61M 5/158 | 604/180 |
| 2009/0069750 | A1 * | 3/2009 | Schraga | A61M 5/14248 | 604/539 |
| 2009/0143763 | A1 * | 6/2009 | Wyss | A61M 5/158 | 604/164.11 |
| 2012/0226242 | A1 | 9/2012 | Nielsen | | |
| 2014/0350485 | A1 * | 11/2014 | Sonderegger | B29C 45/1657 | 604/533 |
| 2019/0160258 | A1 | 5/2019 | Kristen | | |

FOREIGN PATENT DOCUMENTS

| | | | | |
|---|---|---|---|---|
| CN | 218529455 | U | 2/2023 | |
| WO | WO01/13754 | A1 | 1/2001 | |
| WO | 2020097552 | A1 | 5/2020 | |
| WO | WO-2025096648 | A1 * | 5/2025 | A61M 5/158 |

* cited by examiner

APPARATUS FOR RETAINING AND SEALING SEPTUM IN INSERTION MECHANISM FOR FLUID DELIVERY DEVICE

This application claims priority to U.S. provisional patent application Ser. No. 63/214,480, filed Jun. 24, 2021, which is hereby incorporated by reference in their entirety.

BACKGROUND

Field

Example embodiments of the present disclosure relate generally to a fluid delivery device such as a medical infusion system, and more particularly to an improved septum and wedge subassembly of a cannula insertion mechanism in a medical infusion system.

Description of Related Art

Infusion pump therapy requires an infusion cannula, typically in the form of an infusion needle or a flexible catheter, that pierces a patient's skin and through which, infusion of a fluid (e.g., a medication such as insulin) takes place. To facilitate infusion therapy, there are generally two types of fluid pumps, namely, conventional pumps and patch pumps.

Conventional pumps require the use of a disposable component, typically referred to as an infusion set, tubing set or pump set, which conveys the fluid (e.g., insulin) from a reservoir within the pump into the skin of the user. The infusion set consists of a pump connector, a length of tubing, and a hub or base from which a cannula, in the form of a hollow metal infusion needle or flexible plastic catheter, extends. The base typically has an adhesive that retains the base on the skin surface during use. The cannula can be inserted onto the skin manually or with the aid of a manual or automatic insertion device. The insertion device may be a separate unit required by the user.

Another type of fluid pump is a patch pump. Unlike a conventional infusion pump and infusion set combination, a patch pump is an integrated device that combines most or all of the fluidic components, including the fluid reservoir, pumping mechanism, needle or cannula, and an insertion mechanism for automatically inserting the needle or cannula, in a single housing which is adhesively attached to an infusion site on the patient's skin, and does not require the use of a separate infusion or tubing set. A patch pump containing insulin, for example, adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted or complications may otherwise occur, such as restriction in the cannula or the infusion site.

As patch pumps are designed to be a self-contained unit that is worn by the patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced as much as possible. One such part is the insertion mechanism for automatically inserting the cannula into the user's skin.

In order to minimize the height of the insertion mechanism, some conventional insertion mechanisms are configured to insert the cannula at an acute angle from the surface of the skin, e.g. 30-45 degrees. However, it may be preferable to insert the cannula perpendicular or close to perpendicular from the surface of the skin, since this would require the minimum length of cannula insertion. In other words, with the minimum length of cannula being inserted into the user's skin, the user can experience greater comfort and fewer complications, such as premature kinking of the cannula.

SUMMARY

In accordance with advantageous aspects of example embodiments of the present disclosure, an improved septum and wedge subassembly is provided for an insertion mechanism for use in a limited space environment (e.g., a patch pump) that can insert a cannula vertically or close to perpendicularly into the surface of a user's skin while minimizing or reducing its height and therefore the overall height of the device that the insertion mechanism is incorporated into such as the patch pump. The improved septum and wedge subassembly can also reduce manufacturing costs of a pump in terms of using fewer parts and requiring fewer assembly process steps for the insertion mechanism.

In accordance with advantageous aspects of example embodiments, a wedge for receiving a septum in a fluid path of a fluid delivery device comprises: a cup portion and a stem portion defining a fluid path therein through which a needle can slidably pass. The cup portion has a circumferential side wall and a proximal opening dimensioned to receive the septum therein and a distal opening to the fluid path defined by the stem portion. The side wall has an inner diameter that is less than an outer diameter of the septum to provide radial compression on the septum and an opening in the septum through which the needle can slide. The cup portion has a retaining edge along the proximal opening of the slide wall. The retaining edge is configured to extend over at least a portion of a proximal surface of the septum that is accessible via the proximal opening and provide an axial force along an axis parallel to the stem portion to retain the septum in the cup portion.

In accordance with advantageous aspects of example embodiments, the retaining edge comprises a rolled retaining edge formed by rolling the retaining edge inwardly with respect to the cup portion and septum received therein, the rolled retaining edge extending a selected distance over the proximal surface of the septum to provide the axial force.

In accordance with advantageous aspects of example embodiments, the cup portion is metal and the retaining edge is coined inwardly with respect to the cup portion to form the rolling retaining edge.

In accordance with advantageous aspects of example embodiments, the retaining edge comprises at least one finger that extends from a portion of the circumferential side wall of the cup portion and that is folded inwardly with respect to the cup portion and septum received therein to form a flanged retaining edge that extends a selected distance over the proximal surface of the septum to provide the axial force.

In accordance with advantageous aspects of example embodiments, the retaining edge comprises a plurality of fingers that are folded inwardly with respect to the cup portion and septum received therein to form a flanged retaining edge comprising portions thereof that extend a selected distance over the proximal surface of the septum to provide the axial force.

In accordance with advantageous aspects of example embodiments, the stem portion has an inner diameter that is less than the inner diameter of the cup portion. For example, the wedge comprises a flared portion joining the cup portion and the stem portion to define the fluid path, the flared portion having a varying inner diameter that decreases distally and varies from less than the inner diameter of the side wall of the cup portion and greater than the inner diameter of the stem portion.

In accordance with advantageous aspects of example embodiments, the stem portion has a catheter secured thereto that is dimensioned to slidably receive the needle.

In accordance with advantageous aspects of example embodiments, the wedge is a unitary piece of material chosen from a malleable metal that is biocompatible with a fluid delivered by the fluid delivery device. For example, the metal is stainless steel.

In accordance with advantageous aspects of example embodiments, the relative dimensions of the cup portion and the septum are selected to provide a needle-septum interface seal from radial compression that can withstand a designated filling pressure for the fluid delivery device. For example, the designated filling pressure is 20-55 pounds per square inch.

In accordance with advantageous aspects of example embodiments, the rolled retaining edge comprises an annular ring shape dimensioned with an outer diameter of 2.8 millimeters (mm) and an inner diameter of 2.4 mm, and the cup portion is dimensioned to have a height between 1.4 m pre-crimp and 1.0 mm post-crimp.

Additional and/or other aspects and advantages of the present invention will be set for in the description that follows, or will be apparent from the description, or may be learned by the practice of the invention. The present invention may comprise a method or apparatus or system having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXAMPLE EMBODIMENTS

Figure 1:
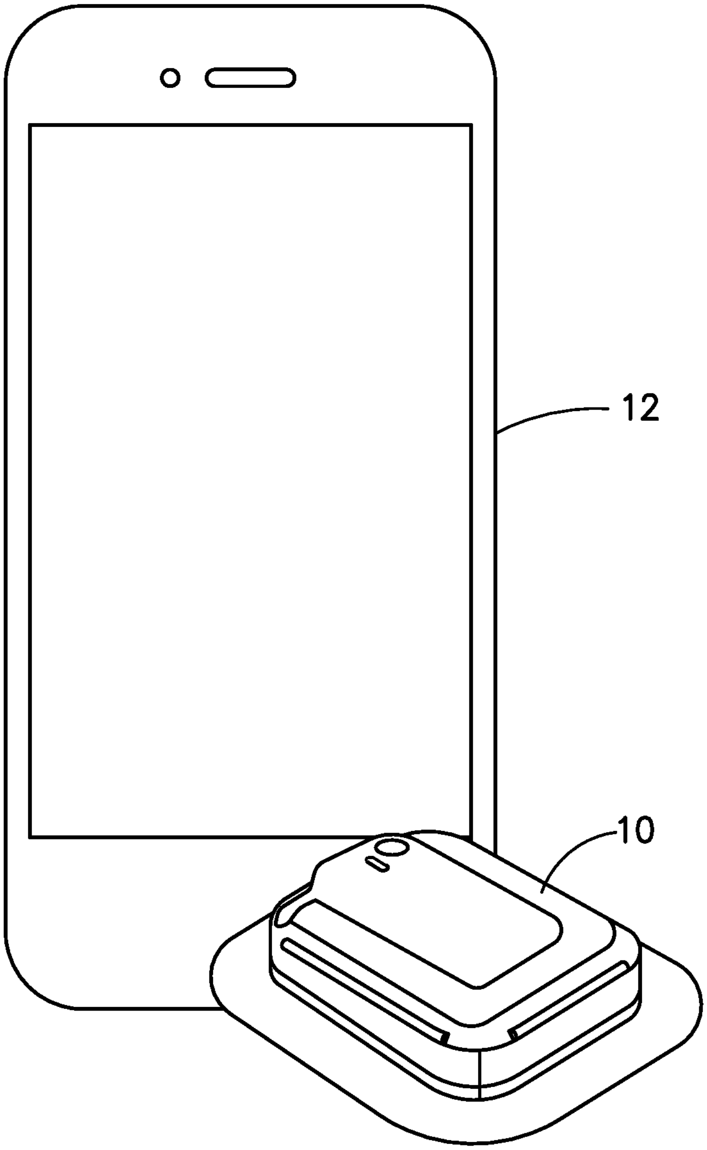
FIG. 1 is a perspective view of an example fluid delivery device and optional wireless controller.

As will be appreciated by one skilled in the art, there are numerous ways of carrying out the examples, improvements, and arrangements of a wedge and septum subassembly of an insertion mechanism in accordance with embodiments disclosed herein. Although reference will be made to the illustrative embodiments depicted in the drawings and the following descriptions, the embodiments disclosed herein are not meant to be exhaustive of the various alternative designs and embodiments that are encompassed by the disclosed technical solutions, and those skilled in the art will readily appreciate that various modifications may be made, and various combinations can be made with departing from the scope of the disclosed technical solutions. For the purposes of the disclosure of example embodiments herein, the terms “cannula” and “catheter” are used interchangeably.

The example embodiments of the present disclosure are of respective septum and wedge subassemblies that can be deployed in an insertion mechanism that is operated to insert a catheter vertically or close to perpendicularly into the surface of a user’s skin to establish a fluid path from a fluid reservoir to the user via the catheter and other components in the fluid path. The example embodiments of the present disclosure are described with reference to an example fluid delivery device such as a wearable patch pump 10 as shown in FIG. 1. The patch pump 10 can be optionally controlled by a remote controller 12 such as a mobile phone with fluid delivery device control app and/or a dedicated wireless controller.

Figure 2:
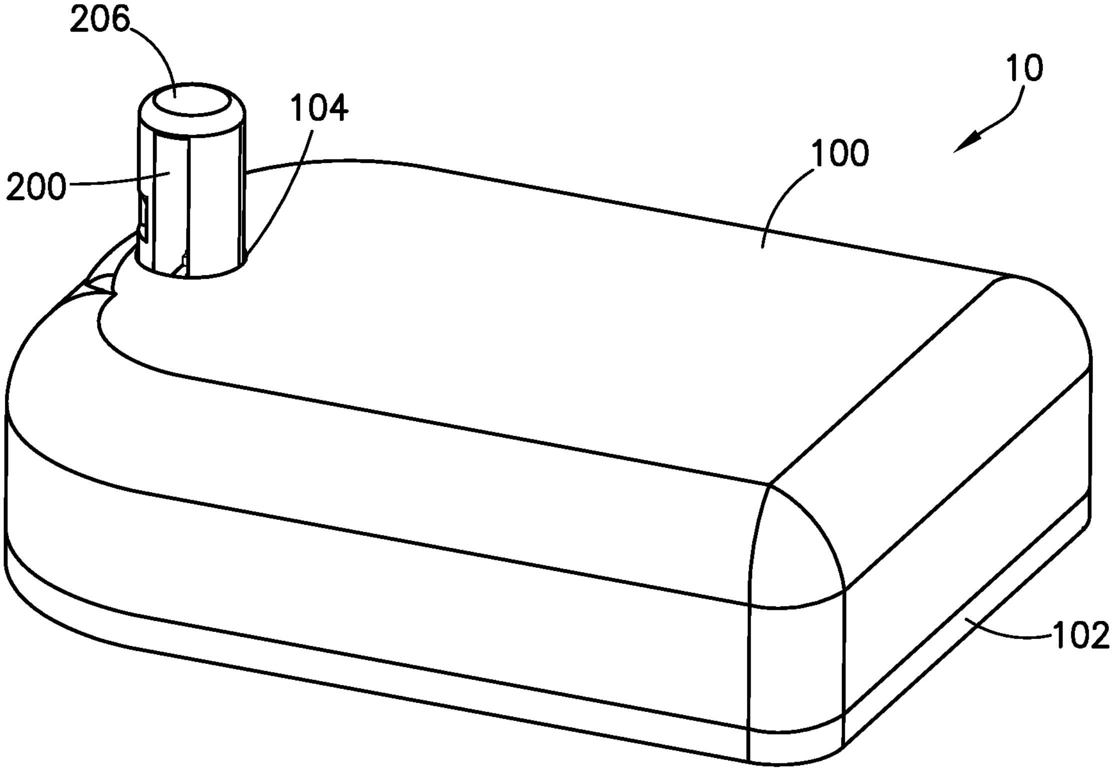
FIGS. 2, 3 and 4 are perspective views of the example fluid delivery device in FIG. 1.
Figure 3:
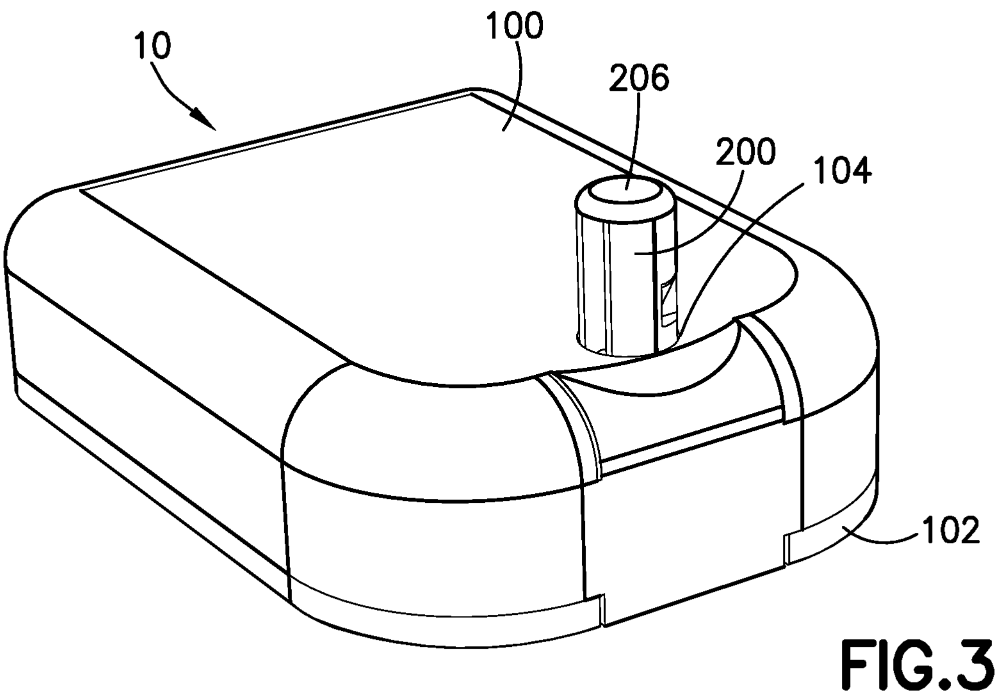
Figure 4:
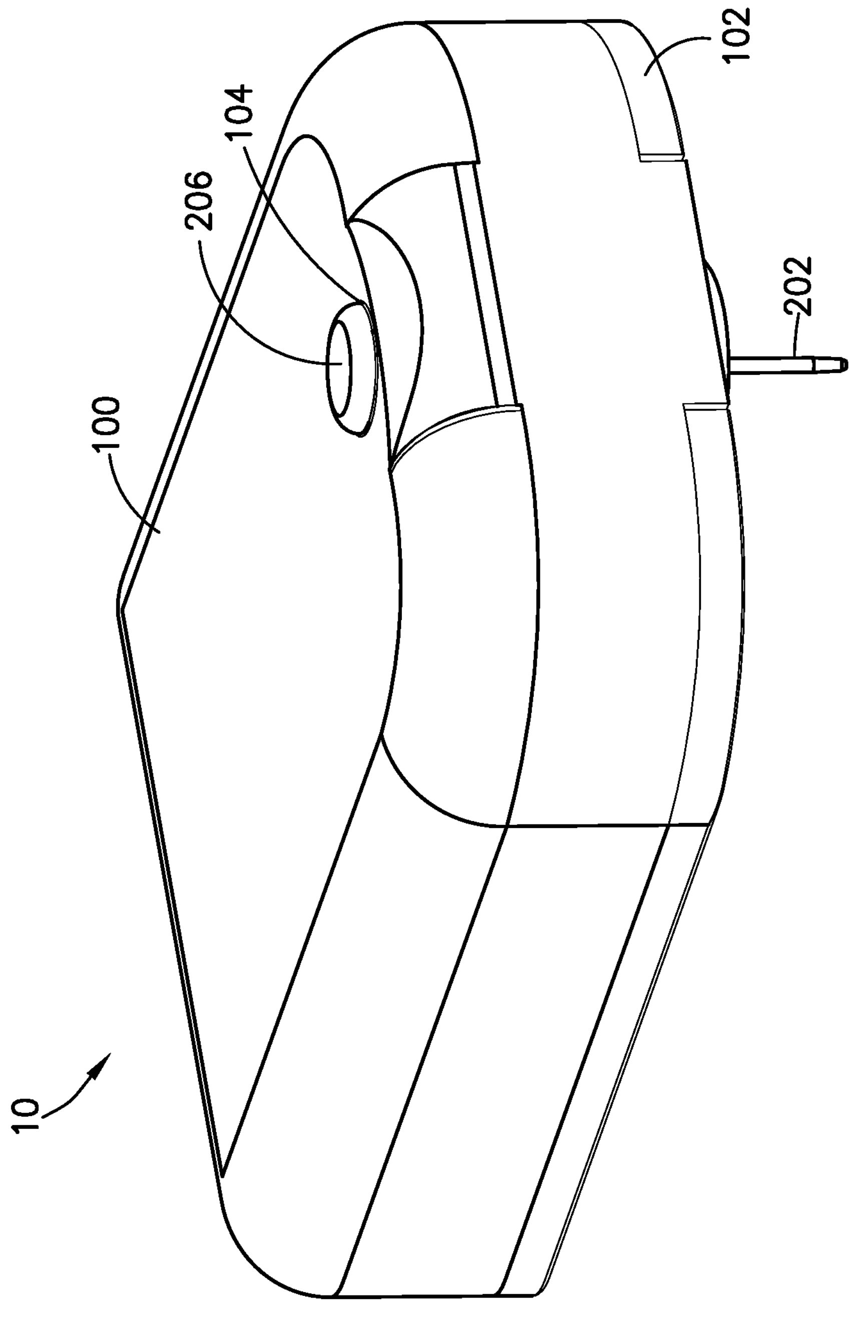

FIGS. 2, 3 and 4 illustrate an example patch pump 10 having a top housing 100 and a base 102. The top housing 100 is shown having an opening 104 through a top surface from which a user-accessible button 206 of a user-actuated insertion mechanism 200 slidably extends. A user can depress the insertion mechanism 200 to deploy a catheter 202 within the insertion mechanism 200 to extend beyond an opening in a bottom surface of the base 102, as described below in connection with FIGS. 5, 6 and 7. FIGS. 2 and 3 show the insertion mechanism 200 before use wherein the insertion mechanism extends beyond the opening 104 through the top surface of the top housing 100. FIG. 4 shows the insertion mechanism 200 after deployment of the catheter wherein the catheter extends from the opening in the bottom surface of the base 102 and into the skin of a patient wearing the pump 10.

Insertion mechanisms provided for the purpose of establishing a continuous fluid path from a reservoir in a fluid delivery device 10 to an outlet (e.g., catheter 202) require a way to maintain the integrity of the fluid path under various pressures. The most significant of these is the filling pressure, such as when a user fills the device 10 reservoir prior to use. Most insertion mechanisms that use a hollow needle 208 as part of their fluid path (e.g. insertion mechanism 200) also use a septum 214. The septum 214 continuously seals the fluid path even as the needle slides through it 214 during insertion and retraction as illustrated and described below in connection with FIGS. 5-9. The needle-septum interface becomes pressurized during the filling of the device 10 and therefore has a minimum pressure requirement. Failure to maintain this seal leads to leakage of the fluid (e.g., medicament) into the device 10 as the device 10 is filled. As described herein, the septum/wedge subassemblies of the present disclosure (e.g., the septum/wedge subassemblies illustrated in FIGS. 16A-16B and 17A-17B) maintain this seal, while also obviating the need for additional parts, to retain a septum 214 in a wedge 212 such as a release collar 218 and wedge cap 216 described below in connection with FIGS. 5-7, or heat staked release collar 218' with lip 222 described below in connection with FIGS. 8-9.

Figure 5:
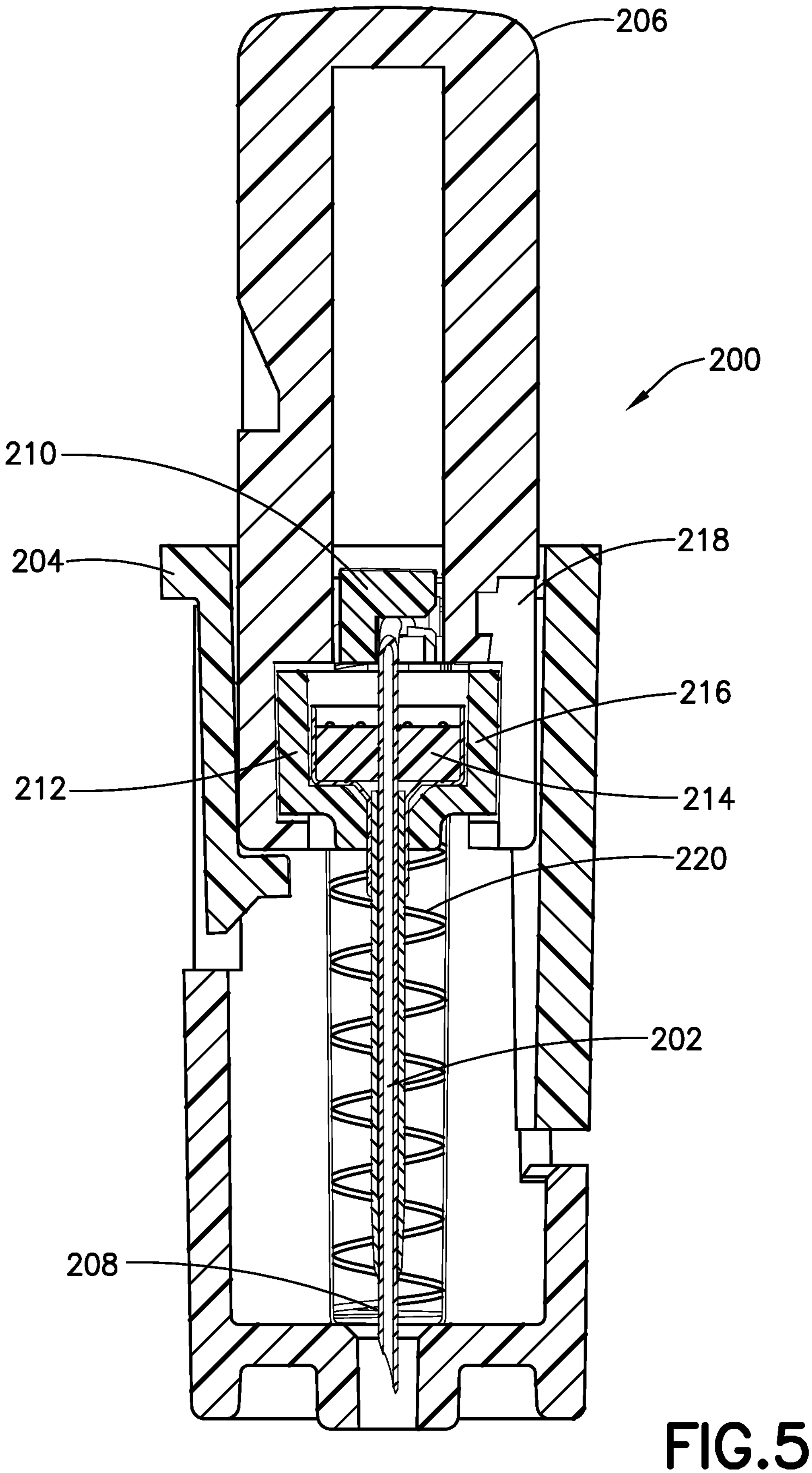
FIGS. 5, 6 and 7 are cross-section side views of an example insertion mechanism that can be used with the example fluid delivery device in FIG. 1.
Figure 6:
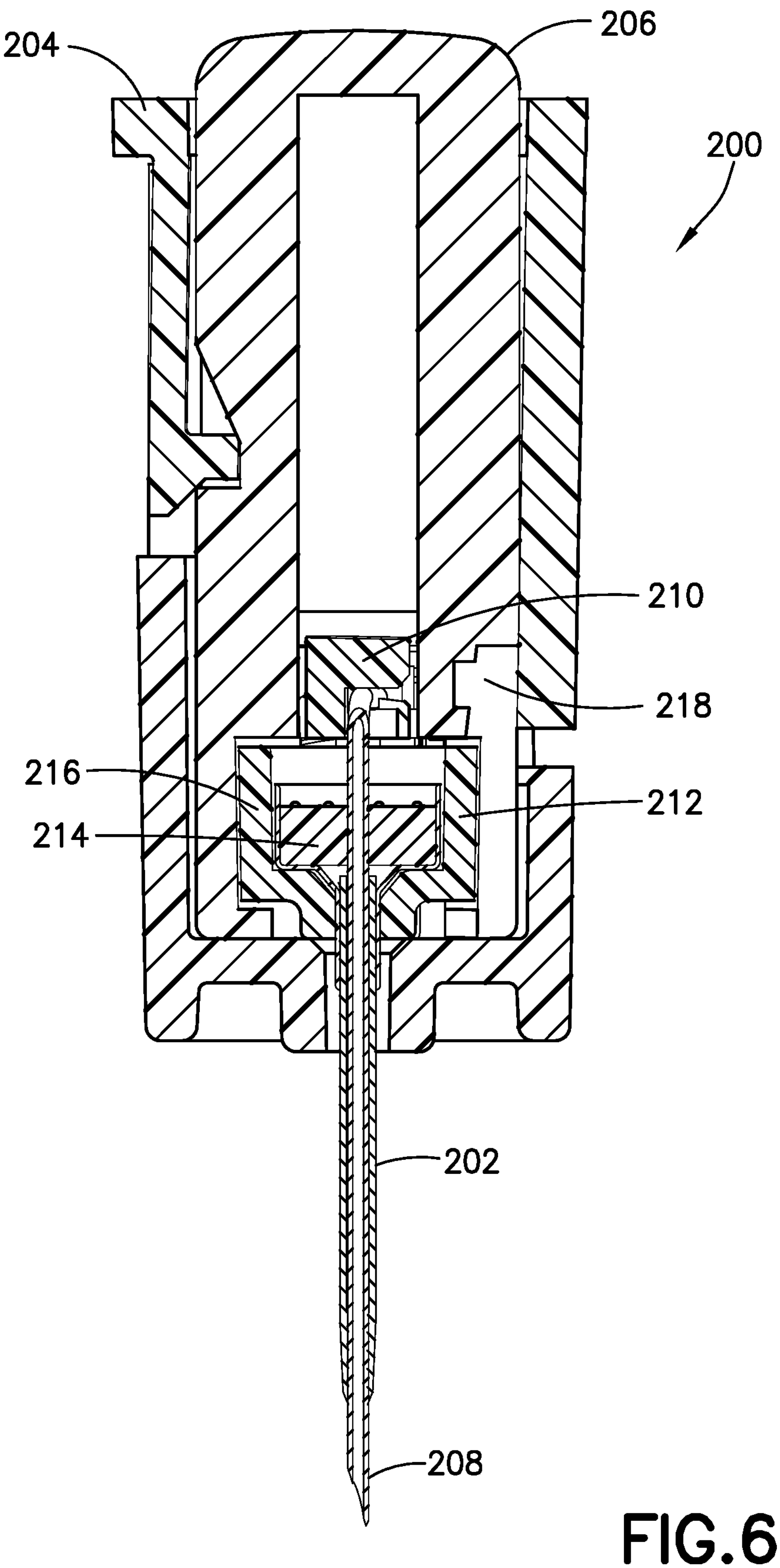
Figure 7:
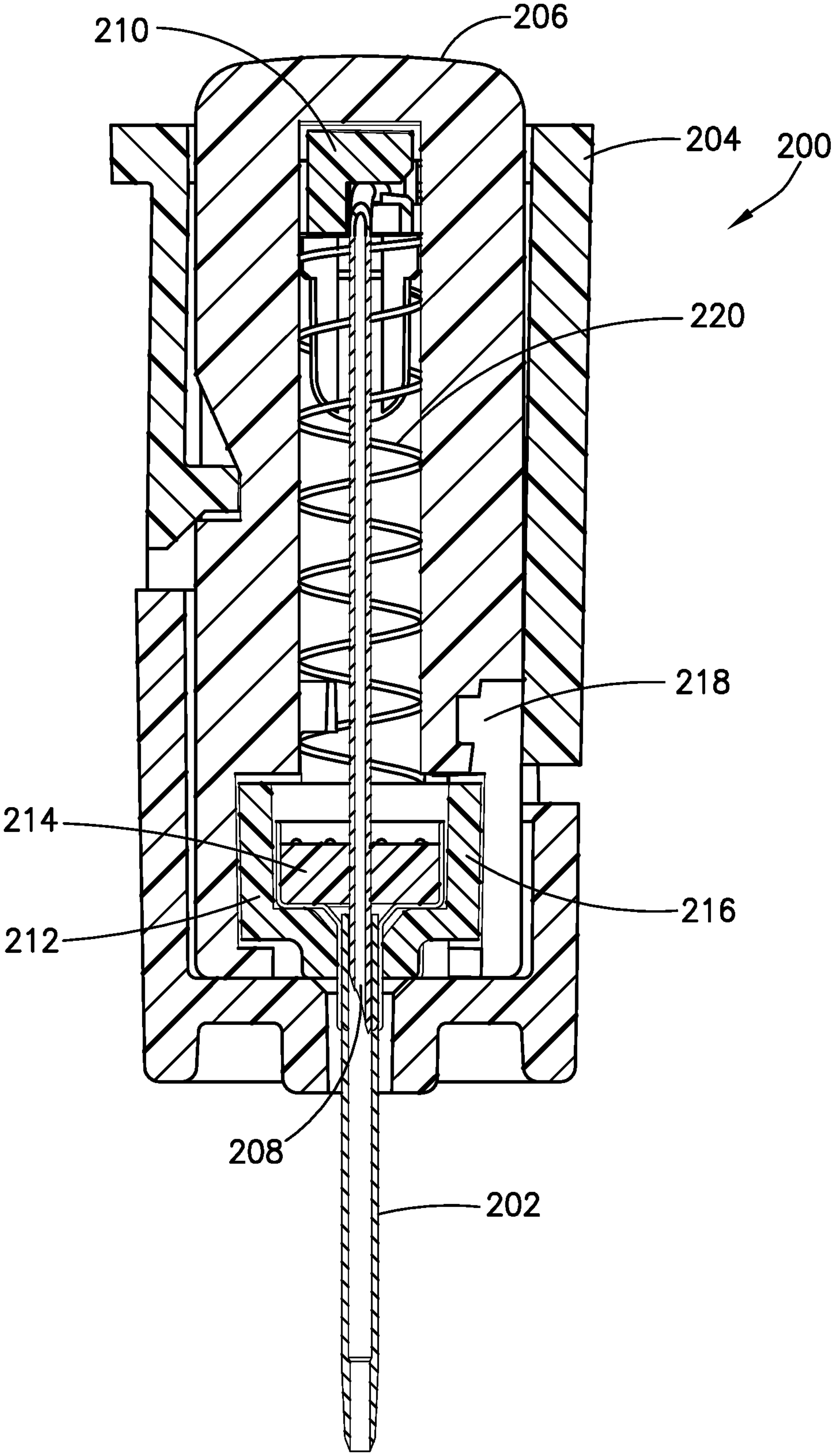

FIGS. 5, 6 and 7 are sectional views of an example insertion mechanism 200 showing, respectively, deployment of a needle 208 and catheter 202 (FIG. 6) from an initial pre-use configuration shown in FIG. 5, and retraction of the needle 208 while leaving the catheter 202 deployed (e.g., inserted into a patient's skin) as shown in FIG. 7. It is to be understood that the example embodiments of septum/wedge subassemblies described herein can be used with other insertion mechanisms than those shown in FIGS. 5-9 and FIGS. 10-12 described herein for illustrative purposes. As described herein, the example embodiments of septum/wedge subassemblies of the present disclosure are advantageous because they retain the septum in the wedge without requiring additional parts (e.g., as shown in FIGS. 5-9) in the insertion mechanism in which the septum and wedge are used, thereby reducing costs associated with additional parts and manufacturing steps. Further, the septum/wedge subassemblies of the present disclosure (e.g., the septum/wedge subassemblies illustrated in FIGS. 16A-16B and 17A-17B) are advantageous because they reduce the height of the septum/wedge subassembly and therefore of the insertion mechanism in which the septum/wedge subassembly is used.

As shown in FIG. 5, the example insertion mechanism 200 is assembled by attaching a catheter 202 on a metal wedge 212, then inserting a septum 214 in the wedge and trapping it between a release collar 218 and a wedge cap 216. The septum 214 is radially compressed by the wedge 212 and axially compressed by the release collar 218 to create a seal between the septum 214 and wedge 212. The catheter 202 can be a 24 G plastic catheter manufactured using FEP, and the release collar 218 and wedge cap 216 can be manufactured using PTEG, but materials of these components are not limited thereto. The wedge 212 can be manufactured using 304 stainless steel, and the septum 214 can be manufactured using isoprene, but embodiments are not limited thereto.

With reference to FIGS. 6 and 7, the needle 208 is connected to an introducer needle hub 210 assembled, for example, by gluing or press-fitting tubing on the non-patient end of the catheter 202 or needle 208, and then placing the needle 208 through the introducer needle hub 210 and snapping it in place using any of grooves, slots or detents provided on the introducer needle hub 210. The introducer needle 208 can be a hollow, 24 G needle or cannula manufactured using 304 stainless steel, and the introducer needle hub 210 can be manufactured using PETG, but embodiments are not limited thereto. When a user wearing the fluid delivery device 10 presses the button 206 of the insertion mechanism 200, a return spring 220 connected to the introducer needle hub 210 is compressed as the needle 208 and catheter 202 are both extended from a bottom surface of the insertion mechanism housing 204 and therefore from a bottom surface of a base 102 of the pump 10 as shown in FIG. 6. The insertion mechanism 200 is configured to then retract the needle 208 via release of the return spring 220, leaving the catheter 202 extended, as shown in FIG. 7.

Figure 9:
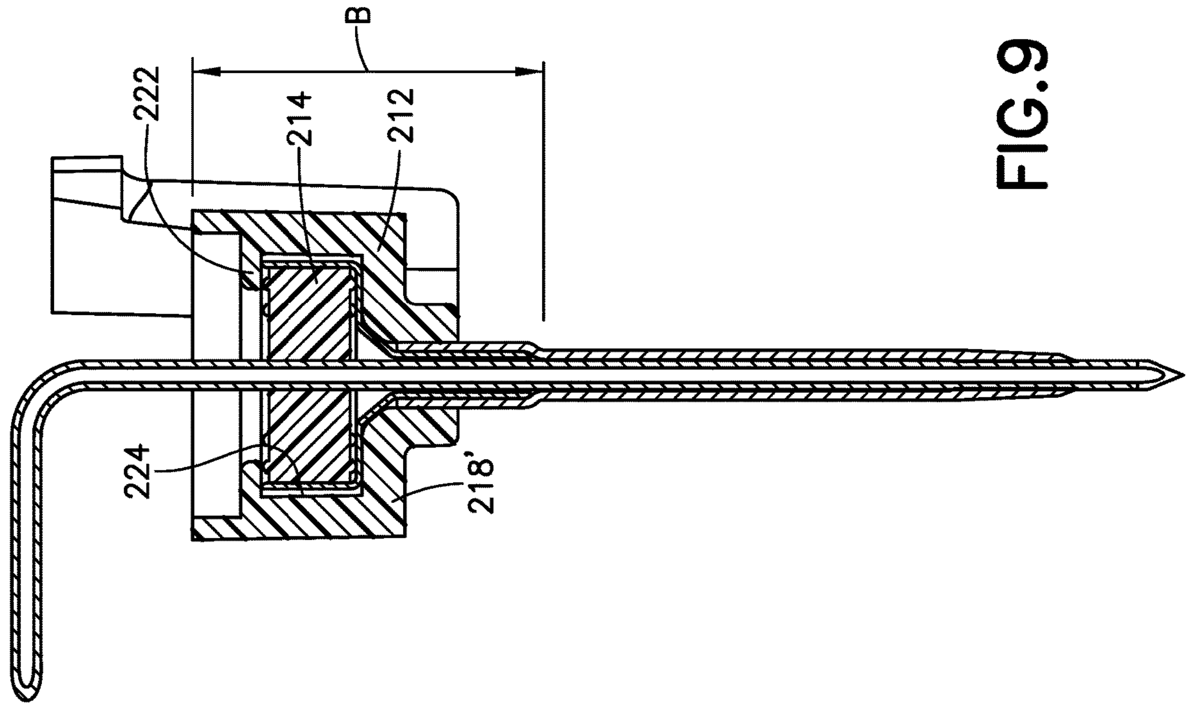
FIGS. 8 and 9 are top perspective and side views, respectively, of an example septum and wedge subassembly that can be used with an example insertion mechanism.
Figure 8:
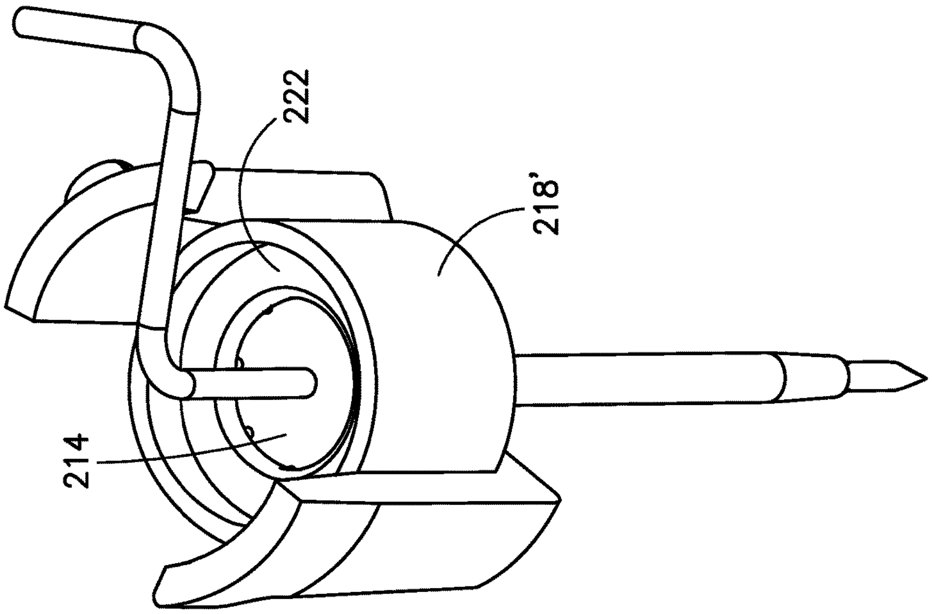

FIGS. 8 and 9 illustrate another example of an insertion mechanism 200' having a different configuration of components (e.g., a release collar 218') for retaining a septum 214 in a wedge 212 wherein the release collar 218' is deformed to retain a septum 214 and wedge 212. Septum 214 is cylindrical in shape. The release collar 218' is heat staked during manufacture to deform the inner surface 224 of the release collar 218' to form a lip 222 that retains the septum 214 and wedge 212 within the release collar 218'. Heat staking is described in further detail, for example, in U.S. Pat. No. 5,135,489, the entire contents of which are hereby incorporated by reference.

The septum/wedge subassemblies of the present disclosure described herein (e.g., the septum/wedge subassemblies illustrated in FIGS. 16A-16B and 17A-17B) obviate the need for additional parts such as the release collar 218 and wedge cap 216, or heat staked release collar 218' with lip 222, to retain a septum 214 in a wedge 212. For illustrative purposes, the example embodiments of septum/wedge subassemblies are described in connection with another example insertion mechanism 300 shown in FIGS. 10, 11 and 12 that does not have additional components apart from a septum 314 and wedge 312 that are dedicated to retaining the septum 314 in the wedge 312.

Figure 10:
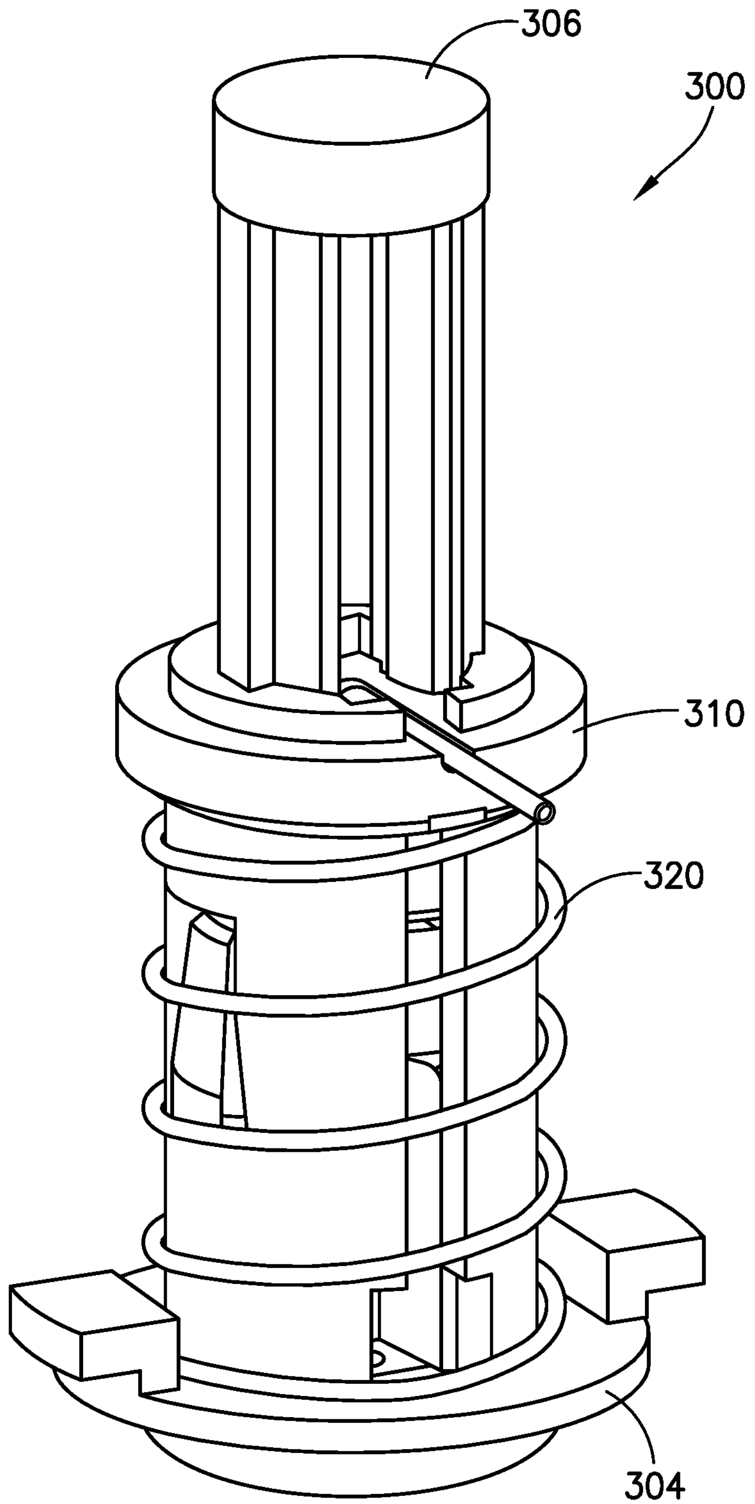
FIGS. 10 and 11 are partial perspective and exploded views, respectively, of another example insertion mechanism improved by a septum and wedge subassembly constructed in accordance with an example embodiment.
Figure 11:
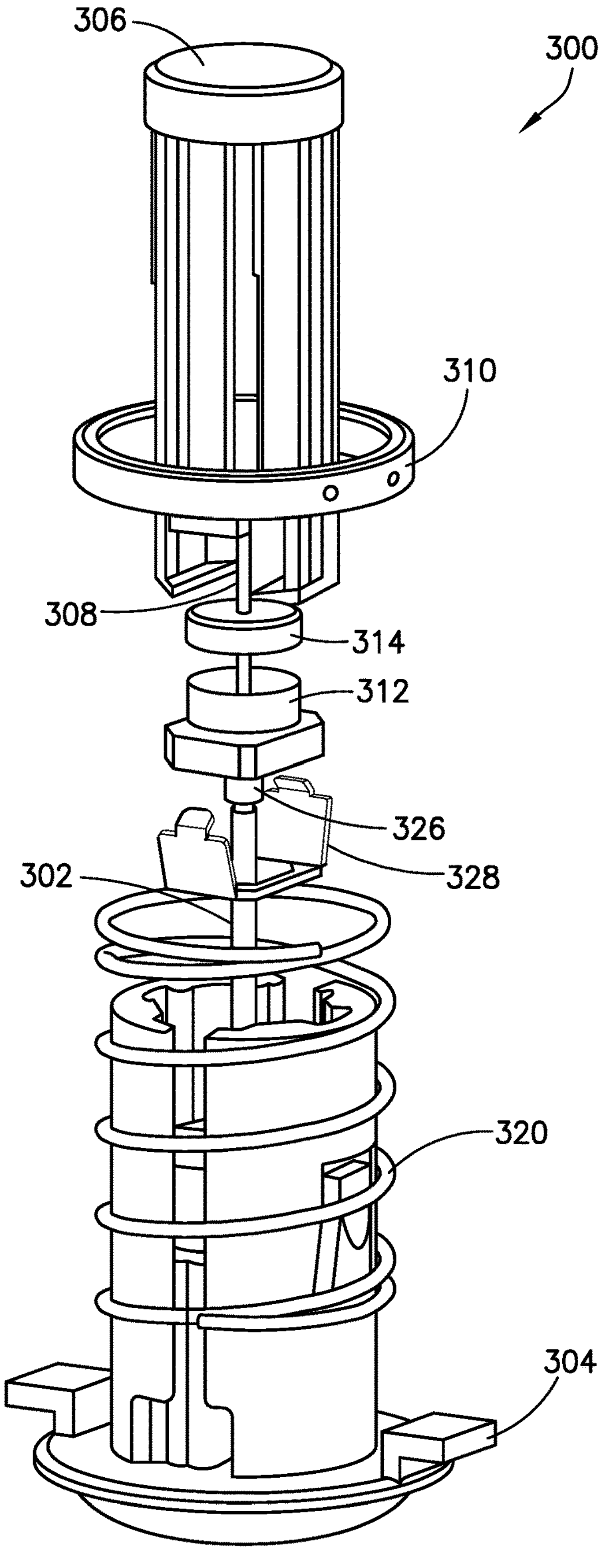
Figure 12:
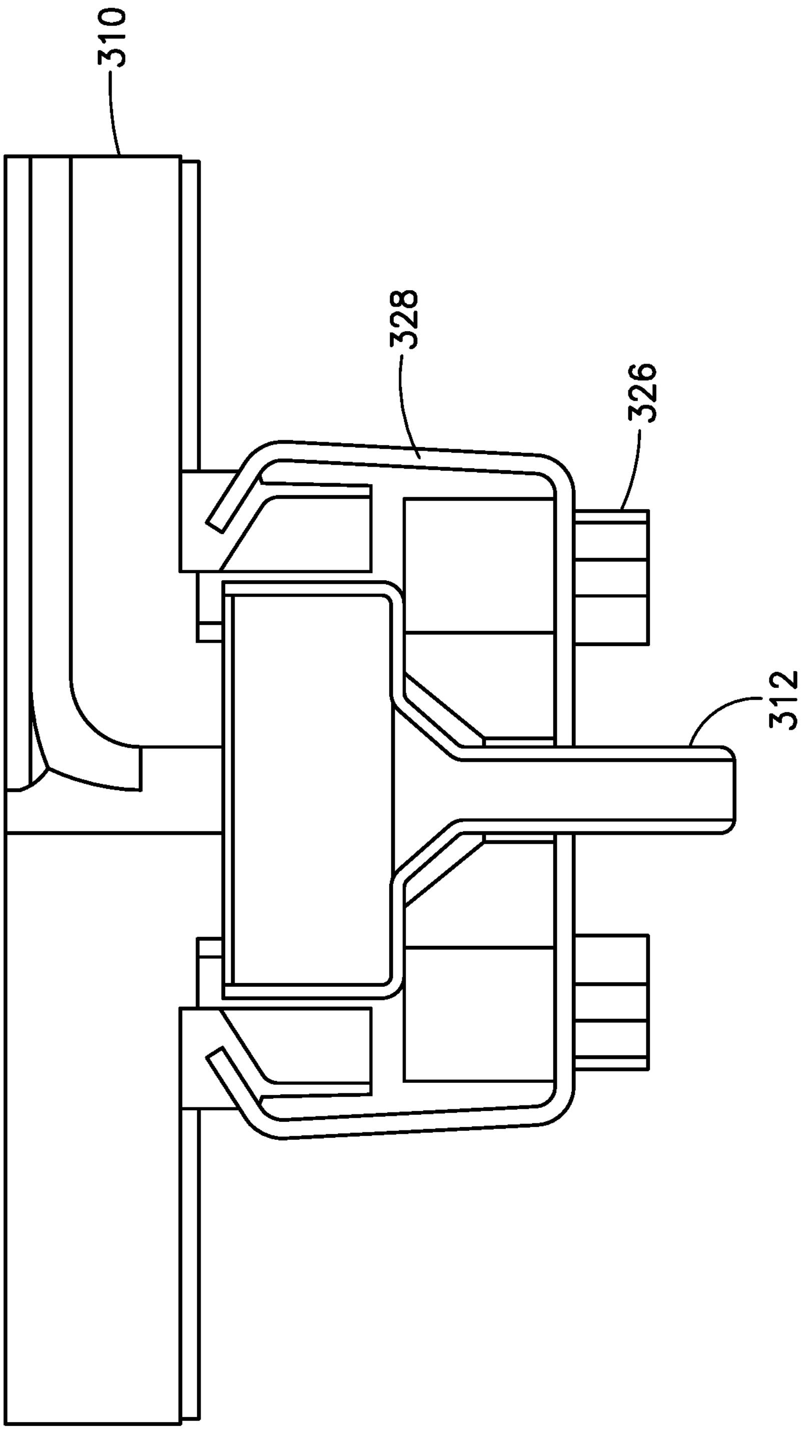
FIG. 12 is a side view of a septum and wedge subassembly constructed in accordance with an example embodiment.

FIG. 10 is a perspective view of the insertion mechanism 300. FIG. 11 is an exploded view illustrating components of the insertion mechanism 300. FIG. 12 is a partial view of the septum 314 and wedge 312 in relation to needle and catheter hubs 310 and 326 when a clip 328 is engaged to retain the needle 308 in the catheter 302 prior to retracting the needle 308. The components of the insertion mechanism 300 illustrated in FIG. 11 are a housing 304, a return spring 320, the catheter hub 326, a cannula 302, the engagement and release clip 328, the septum 314 and wedge 312, needle hub 310, and button 306. As illustrated needle hub 310 surrounds housing 304 and includes openings to permit button 306 to slide relative to the needle hub 310. The engagement and release clip 328 prevents needle hub 310 from separating from catheter hub 326. Once the button 306 has been pressed far enough, the engagement and release clip 328 reaches the distal portion of the housing 304 wherein other housing components permit the engagement and release clip 328 to return to a relaxed position from the engaged position shown in FIG. 12, thereby releasing the needle hub 310 from the catheter hub 326 to retract the needle 314 from the catheter 302. As can be seen in FIG. 12, none of the housing components shown are employed to retain the septum 314 in the wedge 312. Instead, as described below, the wedge 312 is configured to retain the septum 314 independently of other components along the fluid path.

Figure 14A:
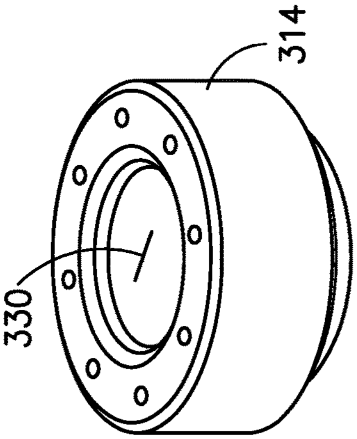
FIGS. 14A and 14B are top and bottom perspective views of an example septum that can be deployed in a septum and wedge subassembly constructed in accordance with an example embodiment.
Figure 14B:
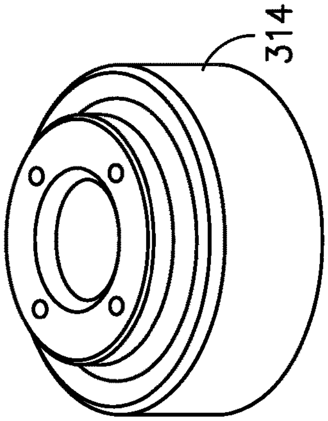
Figure 13:
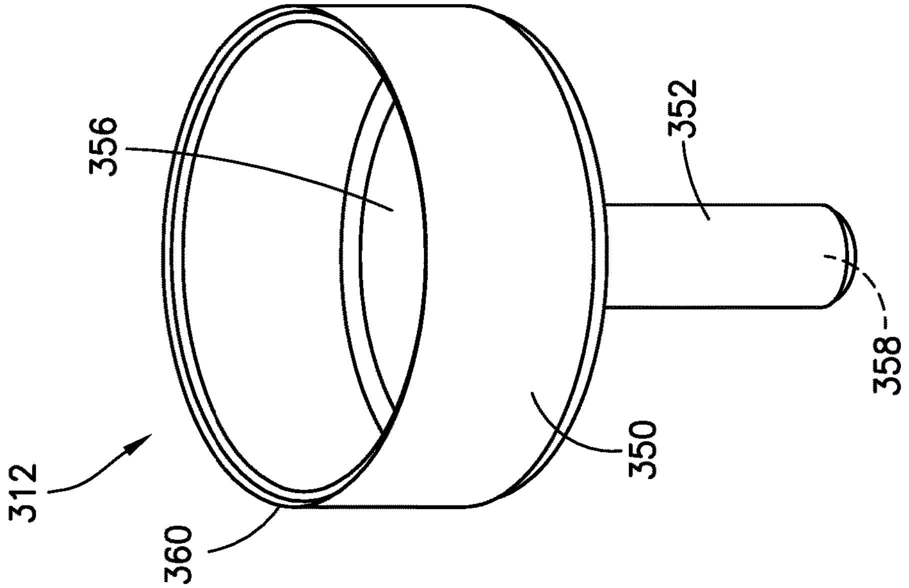
FIG. 13 is a side view of a wedge constructed in accordance with an example embodiment.

FIG. 13 is a perspective view of an example wedge 312 constructed in accordance with an example embodiment and shown prior to receiving a septum 314. FIGS. 14A and 14B are top and bottom views of an example septum 314, which is shown and described in commonly-owned U.S. Pat. Nos.

9,795,777 and D806,241, the entire contents of which are incorporated herein in their entirety. It is to be understood a different septum can be used. With reference to FIGS. 12 and 13, the wedge 312 comprises a cup portion 350 having an inner diameter that is larger than the inner diameter of a stem portion 352, and an optional flared portion 354 disposed therebetween, in a unitary or integral component formed from, for example, 304 stainless steel. Alternatively, the wedge 312 can be configured with a stem portion 352 adjacent the cup portion 350 with no flared portion 354 therebetween. The cup portion 350 has a circumferential wall 351 defining a proximal opening 356 to receive a septum 14. The septum 314 can be formed from an elastomeric material having a low compression set and biocompatibility with the fluid being delivered (e.g., insulin) such as silicone rubber or polyisoprene. The septum 314 can be provided with an aperture or slit 330 into which the needle 308 is introduced and guided through the septum 314 to extend through wedge 312 and into the catheter 302 to provide firmness and sufficient structural integrity to introduce an end of the catheter into a patient's skin prior to retraction of the needle 308. The flared portion 354 can be useful to guide the catheter 302 from the cup portion 350 to the stem portion 352 and out of the distal opening 358 of the wedge 312. The cup portion 350 is dimensioned to be undersized relative to the septum 314 having a smaller inner diameter and circumference relative to the overall diameter and circumference of the septum 14 to place the septum 314 under radial compression and thereby provide a seal between the needle 308 and the septum 314 as the needle is inserted through the septum 314 and slidably engaged therein.

Figure 16B:
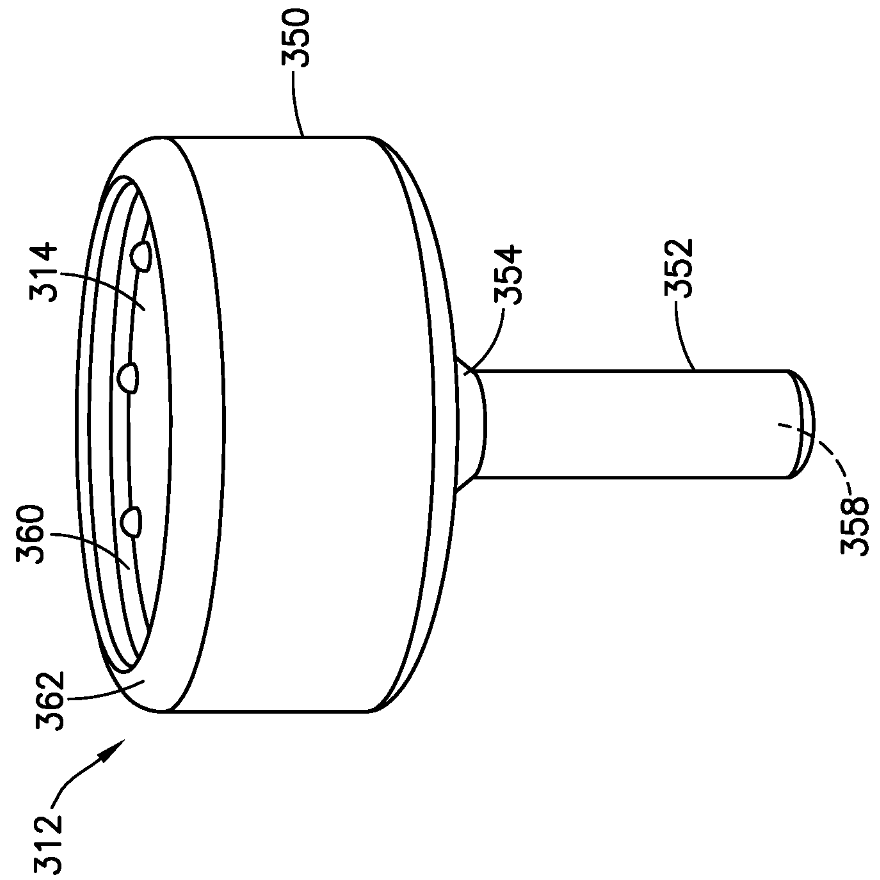
FIGS. 16A and 16B are perspective side views of a septum and wedge subassembly constructed in accordance with an example embodiment.
Figure 16A:
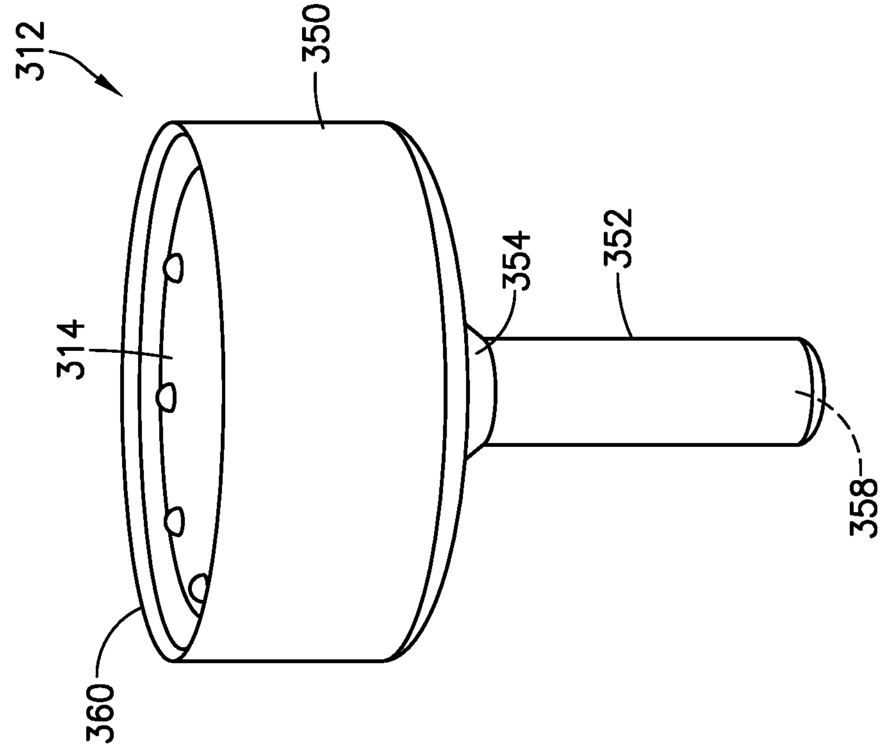

With reference to FIGS. 16A and 16B, a retaining edge 360 on a proximal end of the cup portion 350 of the wedge 312 is formed during assembly of the fluid path to be rolled inwardly over a septum 314 pressed into the cup portion 350 to create a rolled retaining edge 362. For example, the retaining edge 360 can be coined in a selected amount to create a rolled retaining edge 362 that extends over a selected portion of a proximal surface of the septum 314 to provide an axial force along an axis parallel to the stem portion 352 to prevent the septum 314 from sliding out of the cup portion 350 via the proximal opening 356 of the wedge. The formation of the rolled retaining edge 362 can be accomplished via coining, forging or other process to deform the retaining edge 360 into a desired shape to extend over a portion of a proximal surface of a septum 314 provided in the cup portion 350. For example, a rolled edge on the wedge 312 can be formed with an annular ring shape having an outer diameter of 2.82 millimeters (mm) (0.111 inches (in)) and an inner diameter of 2.36 mm (0.093 in), which is sufficient to guard against a fluid pressure of 55 per square inch (psi) on average and including the presence of a needle 308. This amount of rolled edge is correlated to a height difference of 0.254 mm (0.01 in) (i.e., height before crimping and height after crimping). The rolled edge of the wedge 312 is designed to sit above the septum 314 without adding axial compression, but it is possible to crimp to such a height as to compress the septum 314.

The wedge 312 constructed in accordance with the example embodiment in FIGS. 16A and 16B is advantageous because a sealing mechanism is achieved that is contained entirely within two parts, i.e., the wedge 312 and the septum 314. The passive sealing of the fluid path is accomplished by inserting the needle 308 through a rubber septum 14 that is seated within the cup portion 350 of the metal wedge 312. The retention of the septum 314 achieved by the rolled retaining edge 362 and the relatively smaller dimensions of the cup portion 350 as compared to the septum 314 is successful for creation of a seal that can withstand a prescribed filling pressure mentioned above.

Figure 17B:
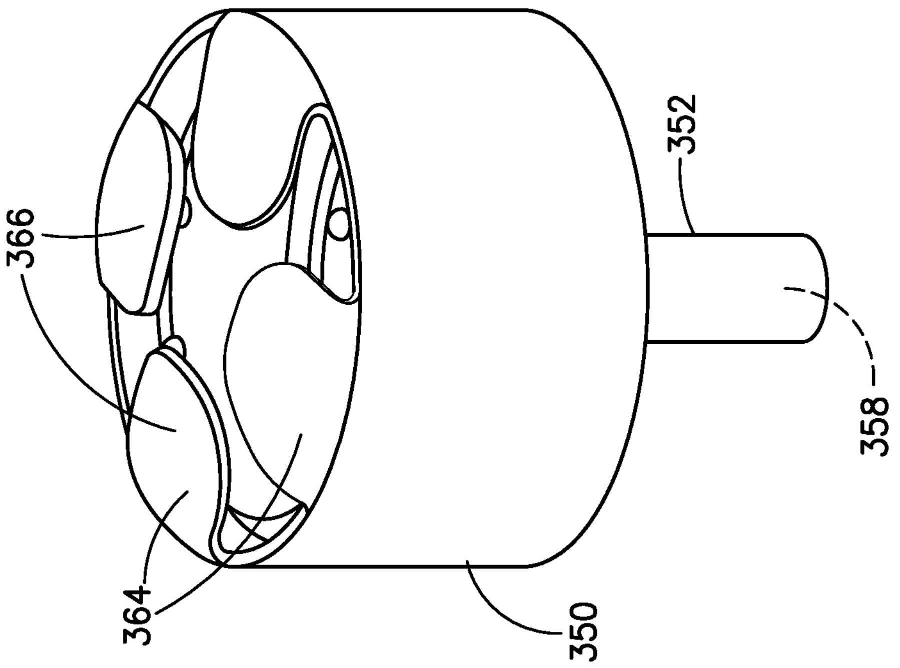
FIGS. 17A and 17B are perspective side views of a septum and wedge subassembly constructed in accordance with another example embodiment.
Figure 17A:
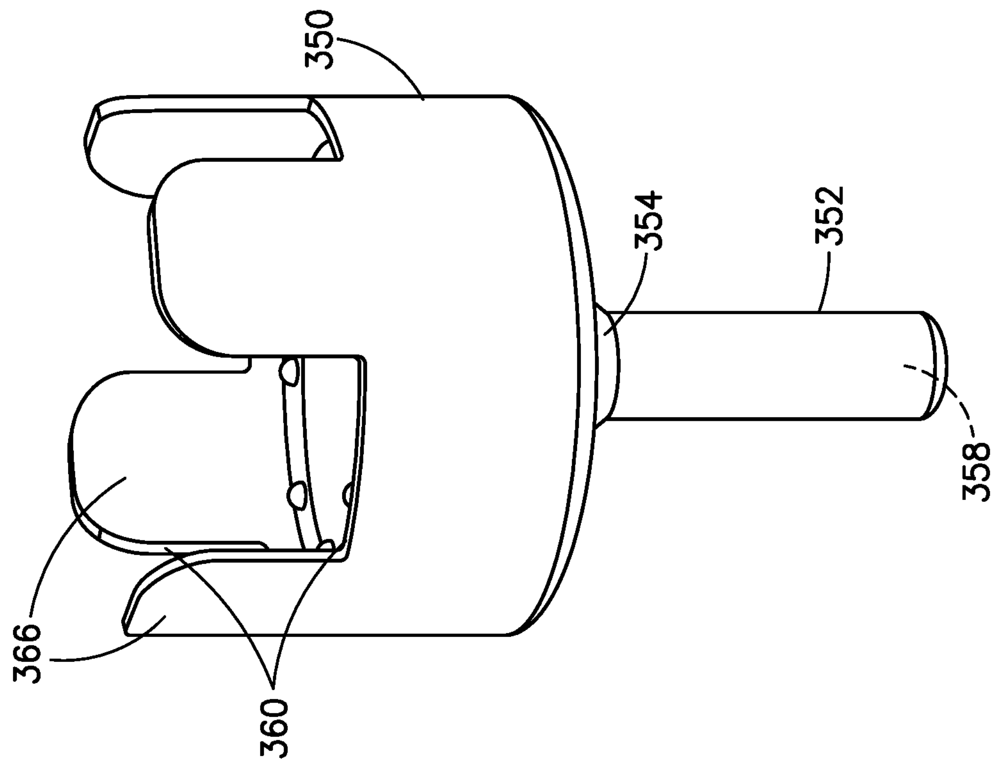

In accordance with another example embodiment shown in FIGS. 17A and 17B, the retaining edge 360 of the wedge 312 can be formed with one or more fingers 366 around the circumference thereof. During assembly of the fluid path, the finger(s) can be folded over to extend along at least a portion of a proximal surface of the septum 314 pressed into the cup portion 350 to create a flanged retaining edge 364 that provides an axial force along an axis parallel to the stem portion 352 to prevent the septum 314 from sliding out of the cup portion 350 via the proximal opening 356 of the wedge. As shown, the retaining edge 362 is provided with four equidistant fingers 366. The width and length of the fingers 366 however can vary. The number of fingers 366 provided along the circumference of the retaining edge 360 of the wedge 312, and the spacing of the fingers, can also vary. The flanged retaining edge 364 is formed to provide the desired axial pressure while also allowing the needle to pass through the proximal surface of the septum 314 and through the distal opening 358 of the wedge 312. The folding of the finger(s) 366 downwards over the septum to create the flanged retaining edge 364 simulates crimping of the rolled retaining edge 362 in the embodiment shown in FIG. 16B whereby a post-folded or post-crimped height of the cup portion 350 of the wedge 312 is achieved that reduces the overall height of the wedge 312 relative to a height "B" shown in FIG. 9 and described below. The side wall of the cup portion 350 of the wedge shown in FIGS. 17A and 17B can also be crimped to reduce the inner diameter thereof to provide radial compression and thereby increase the pressure that can be withstood by the wedge 312 and septum 314 assembly.

Figure 15:
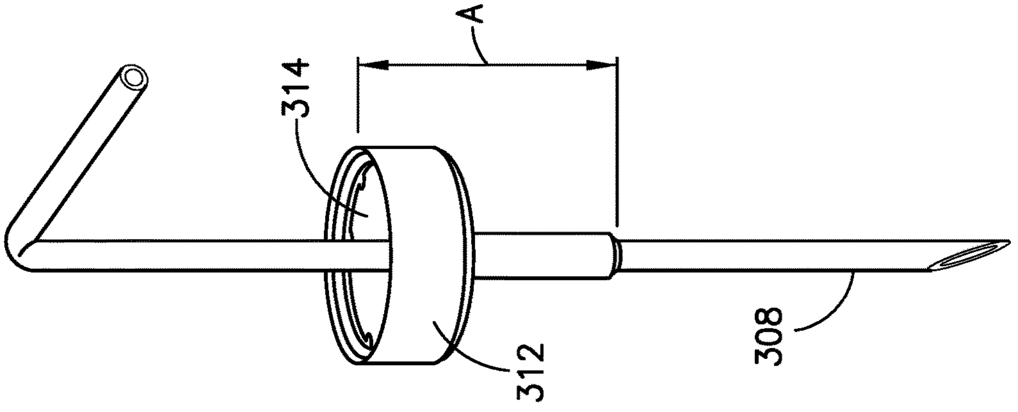
FIG. 15 is perspective view of a septum and wedge subassembly constructed in accordance with an example embodiment with a needle inserted therethrough.

The wedge 312 with a flanged retaining edge 364 constructed in accordance with the example embodiment in FIGS. 17A and 17B is advantageous for the same reasons stated above in connection with the rolled retaining edge 362 such as maintain a desired seal while reducing size, cost and complexity of an insertion mechanism 200 or other fluid path in which the septum 314 and wedge 312 arrangement are deployed. For example, the wedge 312 and septum 314 interface described in accordance with the example embodiments can withstand up to 55 psi of pressure without the need to additional components in the insertion mechanism such as an additional release collar 218, 218' or heat staking. In addition, the height of the insertion mechanism 300 can be reduced since the wedge 312 is configured to perform a dual function of guiding the needle 308 and retaining the septum 314. For example, compare the distance "B" in FIG. 9 with the distance "A" in FIG. 15 (e.g., the height of a release collar 218 and wedge 212 is 6.13 mm (0.241 in), whereas the height of a wedge 312 with rolled retaining edge 362 is 3.47 mm (0.137 in)). While a conventional septum 214 can be press fit into a wedge 212 to provide friction force between the septum and both the base 102 and the wedge, the friction force is not sufficient to maintain the needle 208 and septum 214 seal yet allow the needle 208 to be inserted and retracted relative to the septum 214 without the additional cost and complexity of applying an adhesive, or by swaging plastic material from the base 102 over the top of the septum 214, or providing additional mechanical retention components such as a collar 218 and or heat staking, or a combination of these methods.

With regard to the example wedge 312 described in connection with FIGS. 16A and 16B and FIGS. 17A and 17B, the wedge is formed from a highly malleable material that is biocompatible with the fluid being delivered (e.g., insulin) such as a metal, and can be a selected grade of stainless steel, for example.

The cup portion 350 shown in FIGS. 16A and 16B and FIGS. 17A and 17B can have a depth selected to accommodate a septum of selected height, which can be impacted by the desired length of catheter 302 and need to minimize the height of the insertion mechanism in the housing of the device 10 after the catheter is deployed, assuming the insertion mechanism is not a partially removable device after catheter deployment. The cup portion 350 and the septum 314 can be round. The slit or other opening 330 in the septum 314 is centered with respect to the circumference of the septum 314. Target catheter depth of 6.5 mm (0.256 in) corresponds with typical subcutaneous thickness. Because insertion is perpendicular to the skin surface, the exposed catheter target is 6.5 mm (0.256 in) and within a specified range of 4.5 mm-8.0 mm (0.177 in-0.315 in). The needle 308 can be 28 g with a 0.36 mm (0.014 in) outer diameter or similar dimensions to achieve a balance between providing sufficient flow area and minimized patient pain during insertion. Leak pressure is an important consideration for the implementation of the wedge 312 in accordance with example embodiments. There are two distinct types of leak failures but they are strongly related; that is, leakage at the wedge wall 351 and associated septum 314 pop out, and leakage at the needle 308. The seal around the needle 308 is determined by the radial compression provided by the wedge walls 351 which, in turn, is affected by a range of factors, including septum 314 height.

Actual heights of the wedge cup portion 350 can vary between 1.397 mm (0.055 in) pre crimp and 1.016 mm (0.04 in) post crimp (or pre-fold and post-fold when a finger(s) 366 is employed). It is also possible to use septum heights of 0.80 mm (0.0315 in) pre crimp and 1.016 mm (0.04 in) post crimp; however, the thinner the septum, the less pressure it can withstand on average. With the crimp as described above and a thin septum of original height 0.80 mm (0.0315 in) and original outer diameter of 2.921 mm (0.115 in), and a post crimp wedge cup 350 height of 1.016 mm (0.04 in), the pressure withstood by the wedge 312 and septum 314 assembly is 55 psi on average. An advantageous cup portion 350 height for a pre-crimped wedge 312 is 1.65 mm (0.065 in)+/−0.04 mm (0.0016 in). An advantageous post-crimp cup portion 350 height is 1.44 mm (0.057 in) with a tolerance of 0.05 mm (0.002 in). The post-crimp inner diameter of the cup portion 350 is strongly correlated with leak pressure performance. For example, post-crimp cup portion 350 heights of 1.2-1.55 mm (0.047 in-0.061 in) and post-crimp inner diameters of 2.1-2.5 mm (0.083 in-0.098 in) in the cup portion 350 can provide leak performance from 55-200 psi. Final post-crimp cup portion 350 height and post-crimp cup portion 350 inner diameter are inversely correlated to backpressure performance, that is, the more the wedge 312 is crimped downwards and inwards, the more pressure the wedge 312 and septum 314 assembly can hold. Although various persons, including, but not limited to, a patient or a healthcare professional, can operate or use illustrative embodiments of the present disclosure, for brevity an operator or user is referred to as a "user" herein.

Although various fluids can be employed in illustrative embodiments of the present disclosure, for brevity the liquid in a fluid delivery device is referred to as "fluid" herein.

It will be understood by one skilled in the art that this disclosure is not limited in its application to the details of construction and the arrangement of components set forth in the above description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims.

The invention claimed is:

1. A septum and wedge assembly for a fluid delivery device comprising:

a septum; and a wedge comprising:

a cup portion and a stem portion defining a fluid path;

the cup portion being a unitary, integral component formed from a metal and having a continuous, circumferential side wall and a proximal opening dimensioned to receive the septum therein and a distal opening to the fluid path defined by the stem portion, the side wall having an inner diameter that is less than an outer diameter of the septum to provide radial compression on the septum;

wherein the cup portion has a retaining edge along the proximal opening of the side wall, the retaining edge being configured to extend over at least a portion of a proximal surface of the septum that is accessible via the proximal opening and provide an axial force along an axis parallel to the stem portion to retain the septum in the cup portion.

2. The septum and wedge assembly of claim 1, wherein the retaining edge comprises a rolled retaining edge formed by rolling the retaining edge inwardly with respect to the cup portion and septum received therein, the rolled retaining edge extending a selected distance over the proximal surface of the septum to provide the axial force.

3. The septum and wedge assembly of claim 2, wherein the retaining edge is coined inwardly with respect to the cup portion to form the rolled retaining edge.

4. The septum and wedge assembly of claim 1, wherein the retaining edge comprises at least one finger that extends from a portion of the circumferential side wall of the cup portion and has a width less than a circumference of the circumferential side wall, and that is folded inwardly with respect to the cup portion and septum received therein to form a flanged retaining edge that extends a selected distance over the proximal surface of the septum to provide the axial force.

5. The septum and wedge assembly of claim 1, wherein the retaining edge comprises a plurality of fingers that are folded inwardly with respect to the cup portion and septum received therein to form a flanged retaining edge comprising portions thereof that extend a selected distance over the proximal surface of the septum to provide the axial force.

6. The septum and wedge assembly of claim 1, wherein the stem portion has an inner diameter that is less than the inner diameter of the cup portion.

7. The septum and wedge assembly of claim 6, wherein the wedge comprises a flared portion joining the cup portion and the stem portion to define the fluid path, the flared portion having a varying inner diameter that decreases distally and varies from less than the inner diameter of the side wall of cup portion and greater than the inner diameter of the stem portion.

8. The septum and wedge assembly of claim 1, further comprising a needle, wherein the stem portion has a catheter secured thereto that is dimensioned to slidably receive the needle.

9. The septum and wedge assembly of claim 1, wherein the wedge is a unitary piece of material chosen from a malleable metal that is biocompatible with a fluid delivered by the fluid delivery device.

10. The septum and wedge assembly of claim 9, wherein the metal is stainless steel.

11. The septum and wedge assembly of claim 1, wherein the fluid path of the wedge is fluidically connected to a fluid path from a reservoir of the fluid delivery device, and wherein relative dimensions of the cup portion and the septum are selected to provide a needle-septum interface seal from radial compression that can withstand a designated filling pressure introduced to the fluid path of the wedge when the reservoir in the fluid delivery device undergoes filling.

12. The septum and wedge assembly of claim 11, wherein the designated filling pressure is 20-55 pounds per square inch.

13. The septum and wedge assembly of claim 2, wherein the rolled retaining edge comprises an annular ring shape dimensioned with an outer diameter of 2.8 millimeters (mm) and an inner diameter of 2.4 mm, and the cup portion having the septum therein is subjected to crimping and is dimensioned to have a height between 1.4 mm before the crimping and 1.0 mm after the crimping.

14. The septum and wedge assembly of claim 1, wherein the cup portion having the septum therein is subjected to additional compression in at least one of two directions chosen from being compressed axially to achieve a designated height and being compressed radially to achieve a designated inner diameter.

15. The septum and wedge assembly of claim 14, wherein the additional compression comprises the cup portion undergoing an axial compression such that the cup portion has a height prior to the axial compression of 1.6 millimeters (mm) with a tolerance of 0.04 mm, and the height of the cup portion after the axial compression is 1.4 mm with a tolerance of 0.05 mm.

16. The septum and wedge assembly of claim 14, wherein the additional compression comprises the cup portion undergoing a radial compression such that the outer diameter of the septum is 3 millimeters (mm), the cup portion has an inner diameter less than the outer diameter of the septum prior to the radial compression, and the inner diameter of the cup portion is reduced after the radial compression to a diameter chosen from 2.1-2.5 mm.

17. The septum and wedge assembly of claim 8, wherein the needle pierces the septum to align the needle and septum and wedge assembly.

18. The septum and wedge assembly of claim 1, wherein the septum is manufactured from an elastomeric material.

19. The septum and wedge assembly of claim 1, wherein the wedge is manufactured from 304 stainless steel.

20. The septum and wedge assembly of claim 1, further comprising a catheter hub.

* * * * *